United States Patent
Taoka et al.

(10) Patent No.: US 9,529,086 B2
(45) Date of Patent: Dec. 27, 2016

(54) DUST DETECTION APPARATUS AND DUST DETECTION METHOD

(71) Applicant: Panasonic Intellectual Property Management Co., Ltd., Osaka (JP)

(72) Inventors: Hiroki Taoka, Kyoto (JP); Hiroyuki Kayama, Osaka (JP); Ichiro Takei, Tokyo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 14/664,951

(22) Filed: Mar. 23, 2015

(65) Prior Publication Data
US 2015/0293227 A1    Oct. 15, 2015

(30) Foreign Application Priority Data
Apr. 9, 2014   (JP) .................................. 2014-080446

(51) Int. Cl.
*A47L 15/00* (2006.01)
*G01S 17/00* (2006.01)
(Continued)

(52) U.S. Cl.
CPC ............... *G01S 17/58* (2013.01); *A47L 11/00* (2013.01); *A47L 13/50* (2013.01); *A47L 25/00* (2013.01); *B64C 39/024* (2013.01); *G01N 15/06* (2013.01); *G01S 7/4813* (2013.01); *G01S 17/88* (2013.01); *A47L 2201/06* (2013.01);
(Continued)

(58) Field of Classification Search
USPC .... 356/237.1–241.6, 242.1–243.8, 426–431, 356/600–640
See application file for complete search history.

(56) References Cited

U.S. PATENT DOCUMENTS

| | | | | |
|---|---|---|---|---|
| 4,086,632 A | * | 4/1978 | Lions | G01C 21/00 340/286.14 |
| 4,137,751 A | * | 2/1979 | Rhodes | G01V 5/025 73/28.04 |

(Continued)

FOREIGN PATENT DOCUMENTS

| | | |
|---|---|---|
| DE | 202012100128 | 2/2012 |
| JP | 4-160697 | 6/1992 |

(Continued)

OTHER PUBLICATIONS

The Extended European Search Report dated Sep. 3, 2015 for the related European Patent Application No. 15160748.8.

*Primary Examiner* — Tri Ton
*Assistant Examiner* — Jarreas C Underwood
(74) *Attorney, Agent, or Firm* — Greenblum & Bernstein, P.L.C.

(57) ABSTRACT

A dust detection apparatus includes a dust measuring unit that measures an amount of dust in air, a controller that determines a moving direction of the dust detection apparatus based on the measured amount of dust or a predetermined dust accumulation position candidate, a flight controller that controls a flight of the dust detection apparatus to the determined moving direction, and a communication unit that sends, to a server, location information of a dust accumulation position determined based on the measured amount of dust and the amount of dust measured by the dust measuring unit at the dust accumulation position.

13 Claims, 8 Drawing Sheets

(51) Int. Cl.
*G01N 15/06* (2006.01)
*G01S 17/58* (2006.01)
*A47L 11/00* (2006.01)
*A47L 13/50* (2006.01)
*A47L 25/00* (2006.01)
*G01S 7/481* (2006.01)
*G01S 17/88* (2006.01)
*B64C 39/02* (2006.01)

(52) U.S. Cl.
CPC .. *B64C 2201/027* (2013.01); *B64C 2201/108* (2013.01); *B64C 2201/12* (2013.01)

(56) References Cited

U.S. PATENT DOCUMENTS

| | | | | |
|---|---|---|---|---|
| 4,221,482 A * | 9/1980 | Macourt | | G01N 21/73 250/DIG. 2 |
| 5,240,207 A * | 8/1993 | Eiband | | G05D 1/0038 244/190 |
| 5,977,885 A * | 11/1999 | Watanabe | | G01C 21/3641 340/988 |
| 7,116,272 B2 * | 10/2006 | Wolf | | A63B 29/021 342/443 |
| 8,178,825 B2 * | 5/2012 | Goossen | | F41G 7/303 244/3.1 |
| 8,473,125 B2 * | 6/2013 | Rischmuller | | A63H 27/12 244/17.13 |
| 8,908,476 B2 * | 12/2014 | Chun | | B63G 8/001 114/312 |
| 9,073,637 B2 * | 7/2015 | Ohtomo | | G05D 1/101 |
| 2003/0033086 A1 * | 2/2003 | Lee | | G01C 11/025 702/5 |
| 2003/0075642 A1 * | 4/2003 | Silansky | | B64B 1/02 244/30 |
| 2004/0143602 A1 * | 7/2004 | Ruiz | | H04N 7/181 |
| 2007/0035730 A1 | 2/2007 | Koshinz | | |

FOREIGN PATENT DOCUMENTS

| | | |
|---|---|---|
| JP | 2533687 B | 9/1996 |
| JP | 10-295604 | 11/1998 |
| WO | 2013/076712 | 5/2013 |

* cited by examiner

FIG. 8

| INDEX | LATITUDE | LONGITUDE | AMOUNT OF DUST ACCUMULATION | DISTANCE FROM USER |
|---|---|---|---|---|
| 1 | x1 | y1 | LARGE | z1 |
| 2 | x2 | y2 | SMALL | z2 |
| 3 | x3 | y3 | LARGE | z3 |
| ⋮ | ⋮ | ⋮ | ⋮ | ⋮ |

DUST DETECTION APPARATUS AND DUST DETECTION METHOD

BACKGROUND

1. Technical Field

The present disclosure relates to a dust detection apparatus and a dust detection method.

2. Description of the Related Art

Automatic indoor cleaning apparatuses have been proposed for automatically cleaning high places, such as a ceiling, a wall, and furniture (for example, see Patent Literature 1). The automatic indoor cleaning apparatus disclosed in Patent Literature 1 has propellers driven by an ultrasonic motor, and moves a body along a ceiling or a wall surface while detecting the ceiling or the wall surface, thereby removing dust (dust particles) that adheres to the ceiling or the wall surface.

Patent Literature 2 proposes a dust measuring apparatus for receiving LED light reflected by dust with a photo diode, and for measuring an amount of dust based on intensity of the light received with the photo diode.

CITATION LIST

Patent Literatures

PTL 1: Unexamined Japanese Patent Publication No. H10-295604

PTL 2: Japanese Patent No. 2533687

SUMMARY

Generally, people who clean a room often overlook dust accumulated on inconspicuous high places, such as on a shelf or on a lampshade. It is difficult even for the automatic indoor cleaning apparatus described in Patent Literature 1 to clean all dust accumulation positions without exceptions. Besides, the dust measuring apparatus described in Patent Literature 2 can only measure the amount of dust in a measuring area.

For example, even if scattered pollen (dust) is detected and removed, when accumulated pollen remains unremoved on a place where cleaning is overlooked, the accumulated pollen scatters again. The scattered pollen will need to be removed again, and will cause people to easily develop a pollen allergy.

Thus, unless a scattering source is specified (from where dust is stirred up), it is difficult to remove dust. Besides, unremoved dust at the scattering source will decrease cleaning efficiency.

One non-limiting and exemplary aspect of the present disclosure is a dust detection apparatus that allows a user to effectively remove dust through detection of a dust accumulation position that can be a dust scattering source. Additional benefits and advantages of one aspect of the present disclosure will be apparent from the present specification and the drawings. The benefits and/or advantages may be individually provided by various aspects and features disclosed in the present specification and the drawings, which need not all be provided in order to obtain one or more of such benefits and/or advantages.

In one general aspect, the techniques disclosed here feature a dust detection apparatus, the dust detection apparatus comprising: a dust measuring unit that measures an amount of dust in air; a controller that determines a moving direction of the dust detection apparatus based on the measured amount of dust or a predetermined dust accumulation position candidate; a flight controller that controls a flight of the dust detection apparatus to the determined moving direction; and a communication unit that sends, to a server, location information of a dust accumulation position determined based on the measured amount of dust, and the amount of dust measured by the dust measuring unit at the dust accumulation position.

These comprehensive or specific aspects may be implemented by a system, a method, an integrated circuit, a computer program, or a computer-readable recording medium, and may be implemented by an arbitrary combination of an apparatus, a system, a method, an integrated circuit, a computer program, and a computer-readable recording medium. The computer-readable recording medium includes a nonvolatile recording medium such as a CD-ROM (Compact Disc-Read Only Memory).

The present disclosure allows a user to effectively remove dust by detecting the dust accumulation position that will be a dust scattering source.

BRIEF DESCRIPTION OF DRAWINGS

FIG. 8 is a diagram illustrating an example of guiding information according to the third exemplary embodiment of the present disclosure.

DETAILED DESCRIPTION OF THE PREFERRED EMBODIMENTS

Exemplary embodiments of the present disclosure will be described in detail below with reference to the drawings.

First Exemplary Embodiment

Figure 1A:
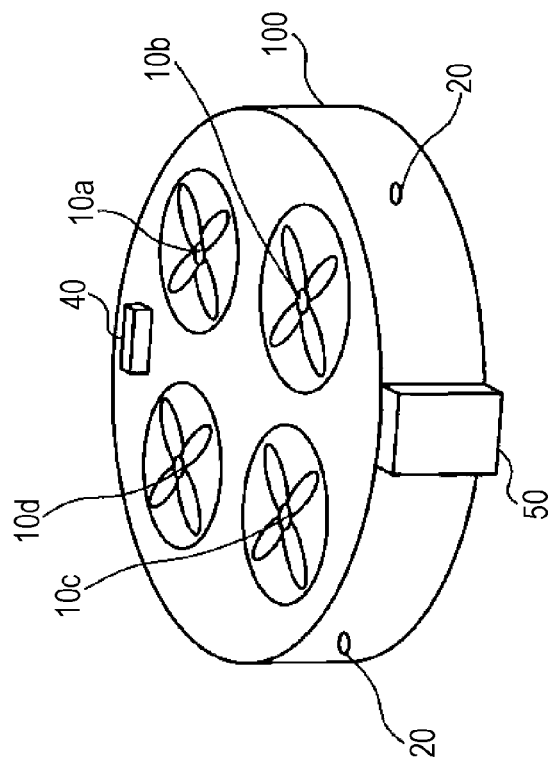
FIG. 1A and FIG. 1B are perspective views each illustrating a dust detection apparatus according to a first exemplary embodiment of the present disclosure.
Figure 1B:
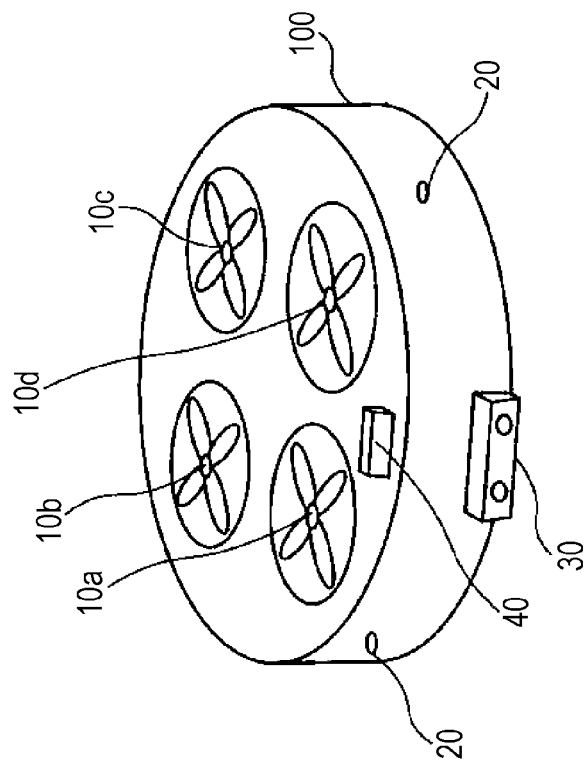

FIG. 1A illustrates a perspective view of dust detection apparatus 100 according to the present exemplary embodiment. FIG. 1B is a perspective view of dust detection apparatus 100 of FIG. 1A viewed from an opposite direction.

As illustrated in FIG. 1A and FIG. 1B, dust detection apparatus 100 includes propellers 10a to 10d, ultrasonic sensors 20, compound eye camera 30, dust collecting unit 40, and GPS (Global Positioning System) receiver 50.

Four thrust propellers 10a to 10d are driven by, for example, an ultrasonic motor (not illustrated). The ultrasonic motor controls a number of rotations of respective propellers 10a to 10d, thereby enabling dust detection apparatus 100 to fly in vertical and horizontal directions. A number of propellers included in dust detection apparatus 100 is not limited to four.

Dust detection apparatus 100 detects a location of an obstacle (such as a ceiling, a wall, or a household utensil (furniture)) in space (for example, an indoor space) with ultrasonic sensors 20 and compound eye camera 30. Dust detection apparatus 100 then controls a flight of dust detection apparatus 100 based on a detection result of the location of the obstacle to avoid a collision between dust detection apparatus 100 and the obstacle. Ultrasonic sensors 20 and compound eye camera 30 may be installed not only on a side of dust detection apparatus 100 as illustrated in FIG. 1A and FIG. 1B, but also in an upper or lower part of dust detection apparatus 100.

Dust collecting unit 40 is an air intake of a dust measuring unit (to be describes later). The dust measuring unit measures an amount of dust in air taken in from dust collecting unit 40. An installation location of dust collecting unit 40 is not limited to an upper part of dust detection apparatus 100 illustrated in FIGS. 1A and 1B, but may be a lower part or a side of dust detection apparatus 100.

GPS receiver 50 acquires location data that indicates a current location of dust detection apparatus 100.

In addition, dust detection apparatus 100 includes an antenna (not illustrated in FIGS. 1A and 1B) for performing communication with a server. For example, dust detection apparatus 100 sends dust information that indicates dust detection results (such as a dust accumulation position and the amount of dust) to the server via the antenna. The server mentioned here may be, for example, included in an indoor home electronics appliance, or may be a cloud server connected to dust detection apparatus 100 via the Internet. The server can be, for example, connected to a device appliance, such as a smart phone, a tablet terminal, a personal computer, or a television provided with a communication function, such as the Internet (may be referred to as a smart TV). The server sends the detection result received from dust detection apparatus 100 to these device appliances. Each of the device appliances can present, to a user, information about how much dust has accumulated at which position by displaying the detection result received from the server.

[Configuration of Dust Detection Apparatus 100]

Figure 2:
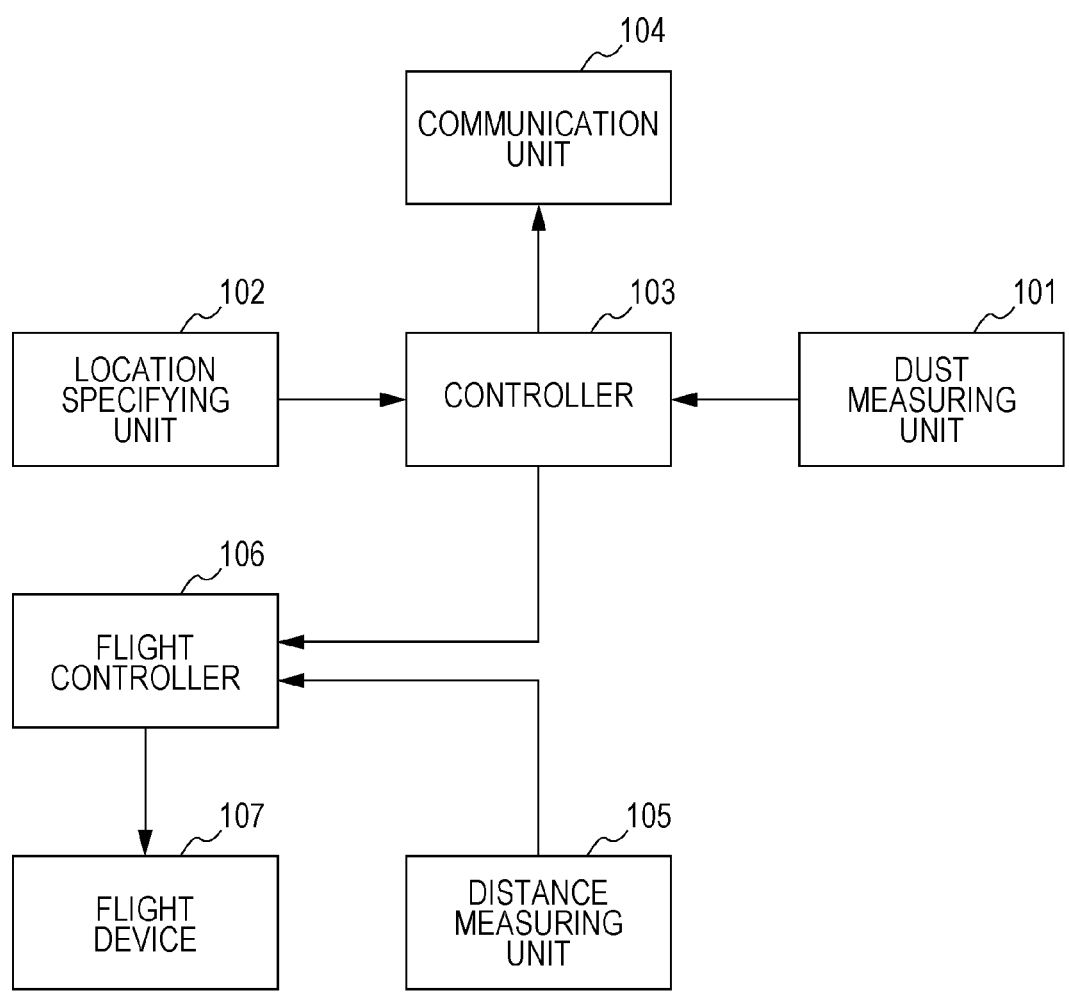
FIG. 2 is a block diagram illustrating a configuration of the dust detection apparatus according to the first exemplary embodiment of the present disclosure.

FIG. 2 is a block diagram illustrating a configuration of dust detection apparatus 100 according to the present exemplary embodiment. Dust detection apparatus 100 illustrated in FIG. 2 includes dust measuring unit 101, location specifying unit 102, controller 103, communication unit 104, distance measuring unit 105, flight controller 106, and flight device 107.

Dust measuring unit 101 measures the amount of dust in the air that is taken in from dust collecting unit 40 illustrated in FIGS. 1A and 1B at the current location of dust detection apparatus 100. For example, dust measuring unit 101 may measure the amount of dust by using a method disclosed in Patent Literature 2. Dust measuring unit 101 outputs a measurement value (dust measurement value) of the amount of dust to controller 103.

Location specifying unit 102 specifies the current location of dust detection apparatus 100, and outputs specified location information to controller 103. Location specifying unit 102 acquires, for example, location data (latitude, longitude) of dust detection apparatus 100 received from GPS receiver 50 illustrated in FIG. 1B. In addition, for example, location specifying unit 102 may include a gyro sensor (not illustrated), detect a motion (behavior) of dust detection apparatus 100, and correct the location data based on a detection result.

Controller 103 uses the dust measurement value received from dust measuring unit 101 to detect the dust accumulation position. Specifically, controller 103 first determines a moving direction of dust detection apparatus 100 from the current location to the dust accumulation position based on the dust measurement value (amount of dust). For example, controller 103 instructs flight controller 106 to move dust detection apparatus 100 to a direction in which the dust measurement value is higher. Controller 103 then determines a position at which the dust measurement value reaches a peak in a path along which dust detection apparatus 100 moves as the dust accumulation position (in other words, a dust scattering source). Controller 103 outputs the location information (for example, latitude, longitude) about dust detection apparatus 100 received from location specifying unit 102, and the dust measurement value at the location, to communication unit 104 as the dust information, the location information corresponding to the location determined as the dust accumulation position.

Communication unit 104 sends the dust information (location information and dust measurement value at the dust accumulation position) received from controller 103, for example, via the antenna to the server.

Distance measuring unit 105 measures a distance between the obstacle (such as a wall or a household utensil) to dust detection apparatus 100 and dust detection apparatus 100, and outputs a measurement result to flight controller 106. Distance measuring unit 105 measures the distance from the obstacle by using, for example, information acquired from ultrasonic sensors 20 or compound eye camera 30 illustrated in FIGS. 1A and 1B.

Flight controller 106 controls a flight (movement) of dust detection apparatus 100 in the moving direction instructed from controller 103. In addition, flight controller 106 controls the flight (movement) of dust detection apparatus 100 based on a distance measuring result received from distance measuring unit 105 to avoid a collision between dust detection apparatus 100 and the obstacle.

Flight device 107 causes dust detection apparatus 100 to fly in accordance with control from flight controller 106. Flight device 107 is, for example, propellers 10a to 10d illustrated in FIGS. 1A and 1B, and the ultrasonic motor that is not illustrated.

[Operation of Dust Detection Apparatus 100]

An operation of dust detection apparatus 100 thus configured will be described.

Figure 3:
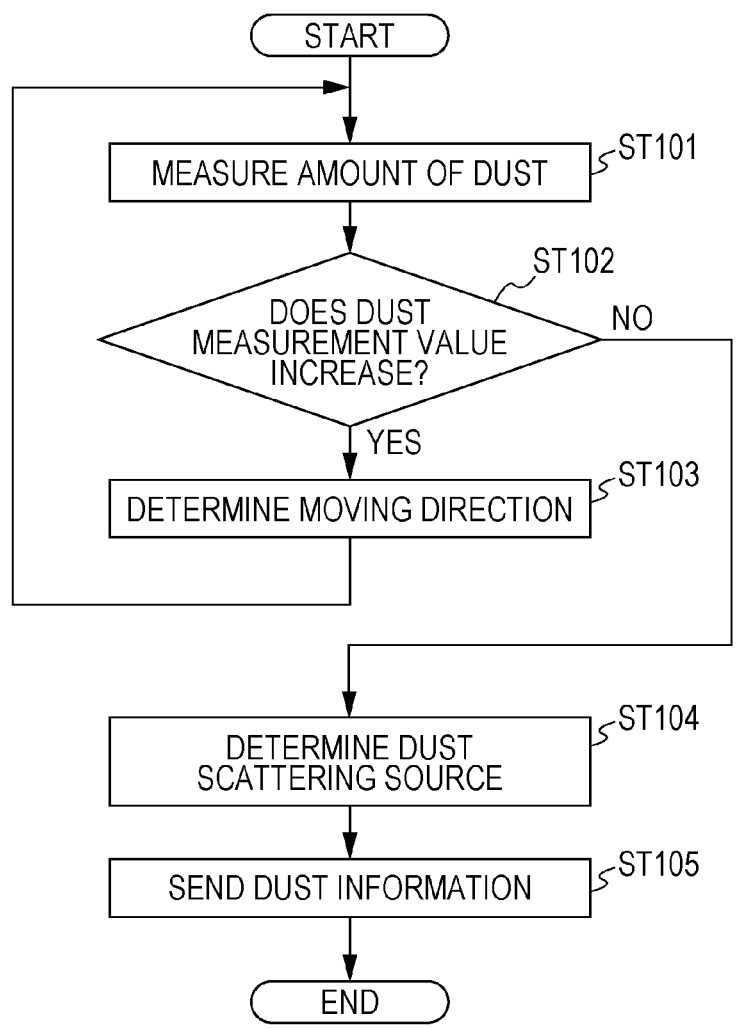
FIG. 3 is a flow chart illustrating an operation of the dust detection apparatus according to the first exemplary embodiment of the present disclosure.

FIG. 3 is a flow chart illustrating a flow of dust detection processing in dust detection apparatus 100.

In FIG. 3, dust measuring unit 101 measures the amount of dust at the current location of dust detection apparatus 100 in step (hereinafter represented as "ST") 101. Dust measuring unit 101 measures the amount of dust in a plurality of directions at the current location of dust detection apparatus 100. For example, dust measuring unit 101 may divide surroundings (360 degrees) of dust detection apparatus 100 into areas of eight directions at intervals of 45 degrees to measure the amount of dust in each area. A number of the above-described areas is not limited to eight, but may include vertical directions.

In ST102, controller 103 determines whether the dust measurement value measured in ST101 increases as compared with the dust measurement value measured last time. That is, controller 103 determines whether the dust measurement value measured this time is higher than the dust measurement value measured last time.

When the dust measurement value measured this time is higher than the dust measurement value measured last time (ST102: Yes), controller 103 determines the moving direction of dust detection apparatus 100 in ST103. Specifically, controller 103 determines, among the plurality of directions measured this time in ST101, the direction in which the dust measurement value is highest as the moving direction of dust detection apparatus 100. Controller 103 provides flight controller 106 with an instruction as to the determined moving direction. Flight device 107 causes dust detection apparatus 100 to fly in accordance with the instruction provided from flight controller 106.

As illustrated in FIG. 3, dust detection apparatus 100 repeats processing of ST101 to ST103 while the dust measurement value measured this time is higher than the dust measurement value measured last time. That is, dust detection apparatus 100 moves in the direction in which the dust measurement value is higher.

On the other hand, in a case where the dust measurement value measured this time is equal to or less than the dust measurement value measured last time (ST102: No), controller 103 determines the current location of dust detection apparatus 100 as the dust accumulation position (dust scattering source) in ST104. Specifically, the case mentioned above where the dust measurement value measured this time is equal to or less than the dust measurement value measured last time refers to a case where the dust measurement value is similar to the dust measurement value measured last time, or where the dust measurement value is less than the dust measurement value measured last time. That is, dust detection apparatus 100 specifies a position at which the dust measurement value reaches a peak by performing processing of ST101 to ST104. In other words, dust detection apparatus 100 searches for a position at which a density of dust in air is higher.

In ST105, controller 103 sends location information that indicates the location determined in ST104 as the dust accumulation position, and the dust information including the dust measurement value at the dust accumulation position, via communication unit 104 to the server.

For example, controller 103 may previously grasp a structure (such as a room, and a size and arrangement of a household utensil installed in the room) of space in which dust detection apparatus 100 can fly. In this case, the dust information may be information that indicates the dust accumulation position and dust measurement value in a three-dimensional map that shows space in which dust detection apparatus 100 can fly.

Alternatively, the server connected to dust detection apparatus 100 may previously grasp the above-described structure of the space in which dust detection apparatus 100 can fly. In this case, the dust information is the location information that indicates the dust accumulation position, and information that indicates the dust measurement value. The server then uses the dust information received from dust detection apparatus 100 to create information that indicates the dust accumulation position and dust measurement value in the three-dimensional map that shows the space in which dust detection apparatus 100 can fly.

The server then presents, to the user, the dust accumulation position and dust measurement value in the space in which dust detection apparatus 100 can fly. For example, the server sends the information that indicates the dust accumulation position and the dust measurement value to the device appliance retained by the user to cause a display unit or the like included in the device appliance to present the information.

Thus, the present exemplary embodiment allows dust detection apparatus 100 to fly, to detect the dust accumulation position that is a dust scattering source, and to send the dust accumulation position to the server. The user can receive presentation of the dust accumulation position and dust measurement value from the server, and can specify how much dust has accumulated at which position. Therefore, the present exemplary embodiment allows the user to effectively remove dust because dust detection apparatus 100 detects the dust accumulation position that is a dust scattering source.

In starting to fly, dust detection apparatus 100 may fly to a dust accumulation position candidate that the user has previously registered in dust detection apparatus 100. In this way, dust detection apparatus 100 can detect the dust accumulation position efficiently. Such a dust accumulation position candidate may be a position that the user wants to always keep clean because the position is clearly visible to an outsider although the position is not clearly visible to the user.

Dust detection apparatus 100 may, before looking for the dust accumulation position by using dust measuring unit 101, previously search for furniture that has a shape in which dust is likely to accumulate by using compound eye camera 30. Since dust is likely to accumulate on furniture having a large cross section when viewed from a vertical direction (such as on a shelf or a lampshade of an electric lamp), grasping existence of such furniture by using the compound eye camera makes it possible to specify the above-described dust accumulation position in a shorter time.

A sensor that can grasp the user's location may be installed at a high location where the sensor can look down the user's motion in a room in which the user lives. Based on the user's location or motion grasped by such a sensor or the like, the dust accumulation position (candidate) can be more effectively specified. For example, a dust accumulation position near a position (for example, near a sofa) where the user stays many hours will increase a risk of the user inhaling dust. Therefore, a motion sensor array may be used that can grasp a person's location as such a sensor, to grasp the position at which the user stays many hours. When the dust accumulation position is found near the position at which the user stays many hours, it is possible to notify the user that the dust accumulation position exists near the position at which the user stays many hours. Furthermore, dust detection apparatus 100 having a sensor capable of grasping a three-dimensional shape like a compound eye camera can also detect existence of the above-described furniture having a large cross section viewed from a vertical direction.

Second Exemplary Embodiment

Figure 4B:
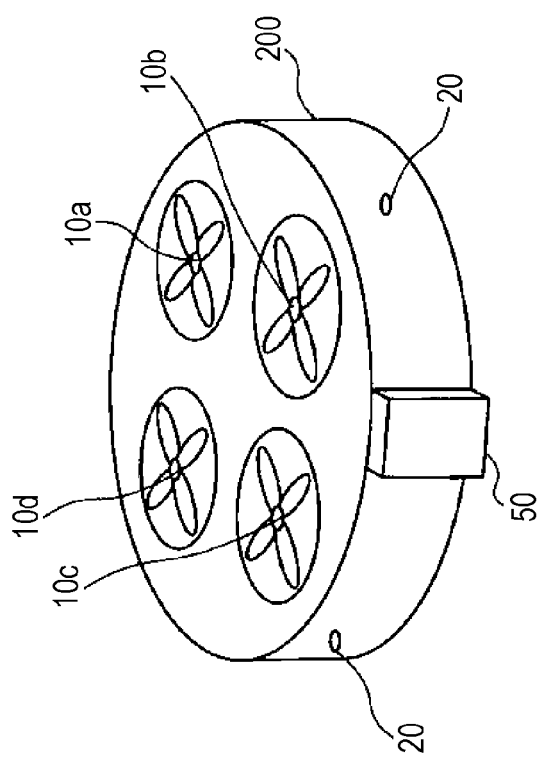
FIG. 4A and FIG. 4B are perspective views each illustrating the dust detection apparatus according to a second exemplary embodiment of the present disclosure.
Figure 4A:
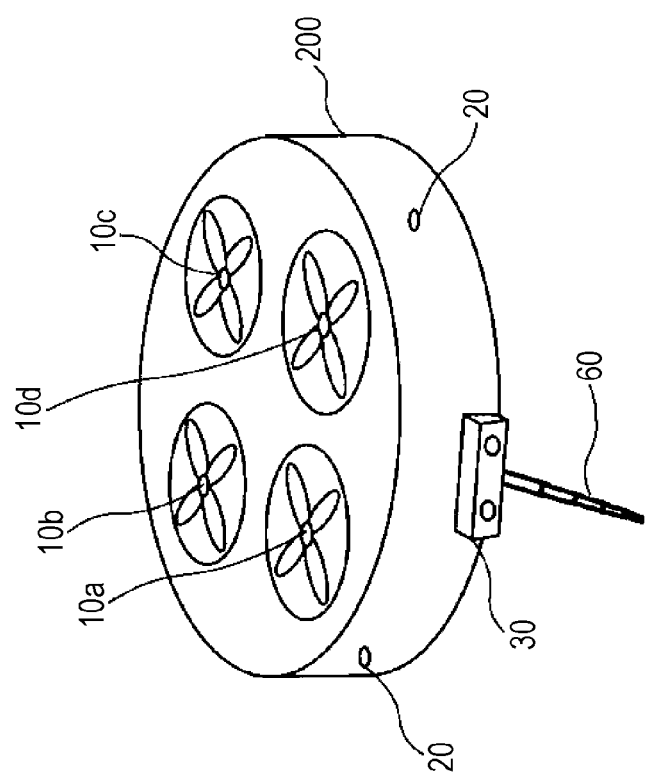

FIG. 4A and FIG. 4B illustrate perspective views of dust detection apparatus 200 according to the present exemplary embodiment. FIG. 4A and FIG. 4B are perspective views of dust detection apparatus 200 viewed from directions opposite to each other. In FIG. 4A and FIG. 4B, components identical to components used in the first exemplary embodiment (FIGS. 1A and 1B) have identical reference symbols, and description of the components will be omitted.

Dust detection apparatus 200 illustrated in FIG. 4A includes dust collecting unit 60 instead of dust collecting unit 40 of the first exemplary embodiment.

Dust collecting unit 60 is an air intake of a dust measuring unit, similar to dust collecting unit 40. However, as illustrated in FIG. 4A, dust collecting unit 60 takes a shape extending like a straw in an obliquely downward direction or in a directly downward direction (not illustrated) of a body of dust detection apparatus 200. Dust collecting unit 60 takes in air from a distal end of the straw-shape into the dust measuring unit. Dust collecting unit 60 may be, for example, extendable, may extend when dust is measured, and may be accommodated in the body in a contracted state when dust is not measured.

For example, dust detection apparatus 200 illustrated in FIG. 4A and FIG. 4B generates an airflow with propellers 10a to 10d, slightly stirs up dust adhering to a measuring object such as a household utensil, and inhales the stirred dust from dust collecting unit 60 to measure an amount of dust.

[Configuration of Dust Detection Apparatus 200]

Figure 5:
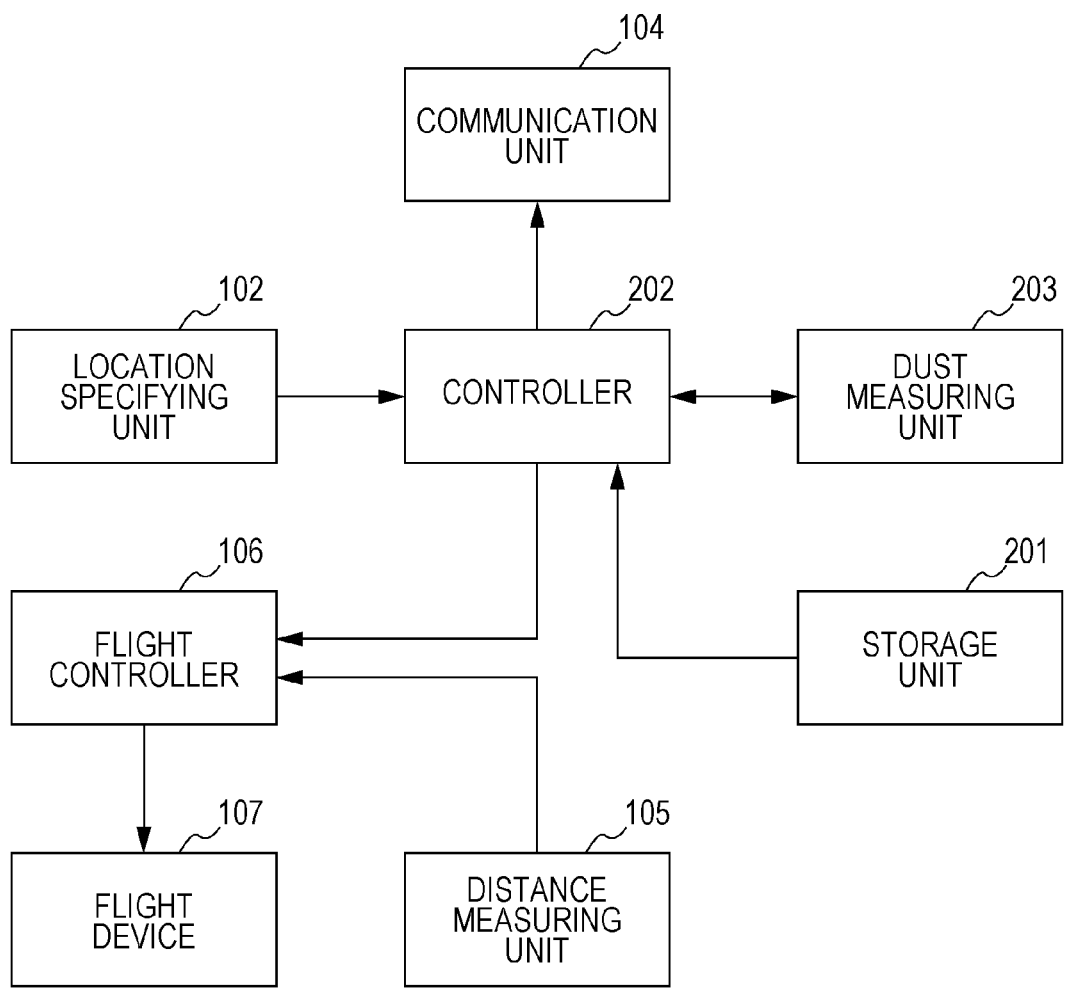
FIG. 5 is a block diagram illustrating a configuration of the dust detection apparatus according to the second exemplary embodiment of the present disclosure.

FIG. 5 is a block diagram illustrating a configuration of dust detection apparatus 200 according to the present exemplary embodiment. In FIG. 5, components identical to components used in the first exemplary embodiment (FIG. 2) have identical reference symbols, and description of the components will be omitted.

In dust detection apparatus 200, storage unit 201 stores location information about positions that are measuring objects at which dust detection apparatus 200 measures the amount of dust. Each of the measuring objects is, for example, a candidate for a dust accumulation position, such as a household utensil in a room. That is, storage unit 201 stores a plurality of positions that are each the candidate for a dust accumulation position. In addition, storage unit 201 stores a measurement altitude during measurement at each of the measuring objects together. The measurement altitude refers to an altitude of dust detection apparatus 200 when dust detection apparatus 200 measures the amount of dust at a measurement location.

The measurement altitude is information for avoiding that dust is stirred up by the airflow generated by dust detection apparatus 200 more than necessary if dust detection apparatus 200 comes too close to the measuring object when dust detection apparatus 200 measures the amount of dust above the measuring object. For example, an altitude that is set as the measurement altitude is an altitude at which airflow intensity on a surface of the measuring object is less than 0.2 m/s during measurement. For example, the measurement altitude is previously measured and stored in storage unit 201.

Controller 202 determines a moving direction of dust detection apparatus 200 from a current location to the dust accumulation position (candidate) based on each of the locations (predetermined candidates for the dust accumulation position) of the measuring objects stored in storage unit 201. Controller 202 instructs flight controller 106 to move dust detection apparatus 200 to the determined moving direction. That is, controller 202 sequentially selects the plurality of positions that are the measuring objects stored in storage unit 201 as the moving direction of dust detection apparatus 200. Controller 202 may instruct flight controller 106 such that dust detection apparatus 200 stays for a while above each of the measuring objects. Dust measuring unit 203 measures the amount of dust at time intervals of about 0.5 second, and notifies controller 202 of a measurement result.

Controller 202 receives notifications of a measurement value (dust measurement value) of the amount of dust from dust measuring unit 203 even during a flight to the sequentially selected measuring objects (candidates for the dust accumulation position). When the dust measurement value exceeds a predetermined amount at some position, the flight to the measuring object is temporarily postponed. First, dust detection apparatus 200 flies in a direction in which the dust measurement value increases, and outputs information about a position at which the dust measurement value reaches a peak to communication unit 104 as the dust accumulation position. Subsequently, the postponed flight to the measuring object is resumed.

[Operation of Dust Detection Apparatus 200]

An operation of dust detection apparatus 200 thus configured will be described.

Figure 6:
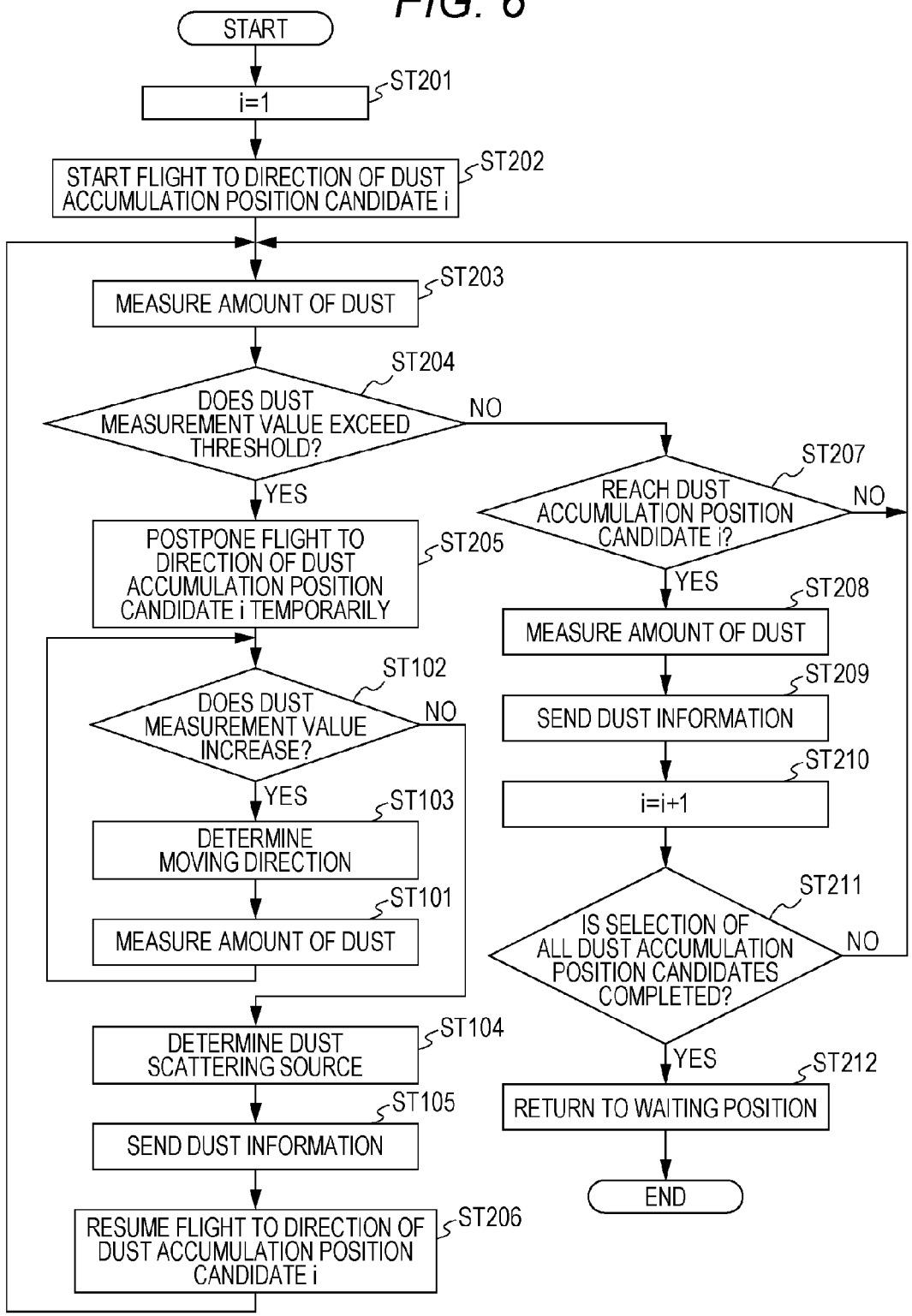
FIG. 6 is a flow chart illustrating an operation of the dust detection apparatus according to the second exemplary embodiment of the present disclosure.

FIG. 6 is a flow chart illustrating a flow of dust detection processing in dust detection apparatus 200. In FIG. 6, processing identical to processing performed in the first exemplary embodiment (FIG. 3) has an identical reference symbol, and description of the processing will be omitted.

In FIG. 6, it is assumed that storage unit 201 of dust detection apparatus 200 previously stores a plurality of (N pieces) of dust accumulation position candidates i (i=1, 2, . . . , N).

In FIG. 6, controller 202 initializes (i=1) an index i of the dust accumulation position candidates in ST201.

In ST202, controller 202 controls flight controller 106 to start a flight to a direction of the dust accumulation position candidate i.

In ST203, dust measuring unit 203 measures the amount of dust at the current location of dust detection apparatus 200 in a same manner as the first exemplary embodiment (dust measuring unit 101).

In ST204, controller 202 determines whether the dust measurement value measured in ST203 exceeds a preset threshold. When the dust measurement value exceeds the threshold (ST204: Yes), controller 202 temporarily postpones the flight to the direction of the dust accumulation position candidate i in order to detect the dust accumulation position near the current location. Controller 202 then performs processing ST101 to ST105 in a same manner as the first exemplary embodiment (controller 103) to detect the dust accumulation position that is a dust scattering source, and sends dust information about the detected dust accumulation position to a server. After the processing of ST101 to ST105 is completed, controller 202 resumes the flight to the direction of the dust accumulation position candidate i in ST206, the flight being postponed in ST205.

On the other hand, when the dust measurement value does not exceed the threshold (ST204: No), controller 202 determines in ST207 whether dust detection apparatus 200 has reached the dust accumulation position candidate i. When dust detection apparatus 200 has not reached the dust accumulation position candidate i (ST207: No), controller 202 continues the flight to the direction of the dust accumulation position candidate i, and returns to processing of ST203.

When dust detection apparatus 200 has reached the dust accumulation position candidate i (ST207: Yes), controller 202 measures the amount of dust at the dust accumulation position candidate i in ST208, and sends the dust information at the dust accumulation position candidate i including the dust measurement value measured in ST208, to the server in ST209.

In ST210, controller 202 increments the index i (i=i+1).

In ST211, controller 202 determines whether selection of all the dust accumulation position candidates has been completed (that is, i>N). When selection of all the dust accumulation position candidates has not been completed (ST211: No), controller 202 starts a flight to a direction of a next dust accumulation position candidate, and returns to processing of ST203.

When selection of all the dust accumulation position candidates has been completed (ST211: Yes), controller 202 controls flight controller 106 to return to a waiting position for dust detection apparatus 200 (ST212).

Thus, dust detection apparatus 200 previously stores the measuring objects that are positions (candidates) that can become the dust accumulation positions, and sequentially measures the amount of dust at the measuring objects. That is, according to the present exemplary embodiment, dust detection apparatus 200 flies, sequentially detects and moves to the dust accumulation position candidates that can become dust scattering sources, and presents the amount of dust at each candidate to the user. This allows the user to check every time a position that the user particularly wants to clean up without exceptions, such as a position at which dust accumulation needs to be particularly avoided, or a position at which dust is highly likely to accumulate.

When the dust measurement value exceeds the threshold, dust detection apparatus 200 temporarily postpones moving to each of the plurality of dust accumulation position candidates stored in storage unit 201, and determines a direction in which the dust measurement value is highest among a plurality of directions as the moving direction, as in the first exemplary embodiment, thereby detecting the dust accumulation position that is a dust scattering source. Thus, according to the present exemplary embodiment, dust detection apparatus 200 detects the dust accumulation position that is a dust scattering source as required even while dust detection apparatus 200 is flying to the previously stored dust accumulation position candidate, so that the user can effectively remove dust, as in the first exemplary embodiment.

In the present exemplary embodiment, a description has been given of a case where dust detection apparatus 200 sends the dust information to the server every time dust detection apparatus 200 measures the amount of dust at each measuring object, as illustrated in FIG. 6. Dust detection apparatus 200 however does not necessarily send the dust information about all the measuring objects to the server every time. For example, dust detection apparatus 200 may send, to the server, the dust information about the measuring object at which the dust measurement value exceeds a predetermined threshold. This allows reduction of an amount of information to be sent from dust detection apparatus 200 to the server. This also allows the server to present to the user the measuring object at which dust has actually accumulated. In addition, the server may compare the dust measurement value with the predetermined threshold.

According to the present exemplary embodiment, dust detection apparatus 200 uses altitude information for controlling altitude of dust detection apparatus 200 during measurement of the amount of dust at the measuring object. Furthermore, dust detection apparatus 200 takes in air near the measuring object by using straw-shaped dust collecting unit 60 illustrated in FIG. 4A during measurement of the amount of dust. This allows dust detection apparatus 200 to measure the amount of dust without scattering dust more than necessary. That is, the present exemplary embodiment can prevent scattering of dust resulting from dust detection apparatus 200.

Third Exemplary Embodiment

In the first exemplary embodiment and the second exemplary embodiment, a description has been given of a case where a dust detection apparatus presents a detected dust accumulation position to a user.

In contrast, high places, such as near a ceiling, are positions where the user tends to overlook accumulation of dust, and are positions the user is unlikely to notice. Accordingly, these positions are inherently hard for the user to recognize, and it is not easy to show these positions to the user accurately in words or by a diagram.

Accordingly, a description will be given of a case where a dust detection apparatus according to the present exemplary embodiment guides the user from a current location of the user to a detected dust accumulation position. Hereinafter, a description will be given of a case where dust detection processing according to the first exemplary embodiment (FIG. 1A to FIG. 3) is performed as an example. However, dust detection processing in the dust detection apparatus according to the present exemplary embodiment is not limited to the processing of the first exemplary embodiment. Processing of the second exemplary embodiment (FIG. 4A to FIG. 6) is also applicable.

[Configuration of Dust Detection Apparatus 300]

Figure 7:
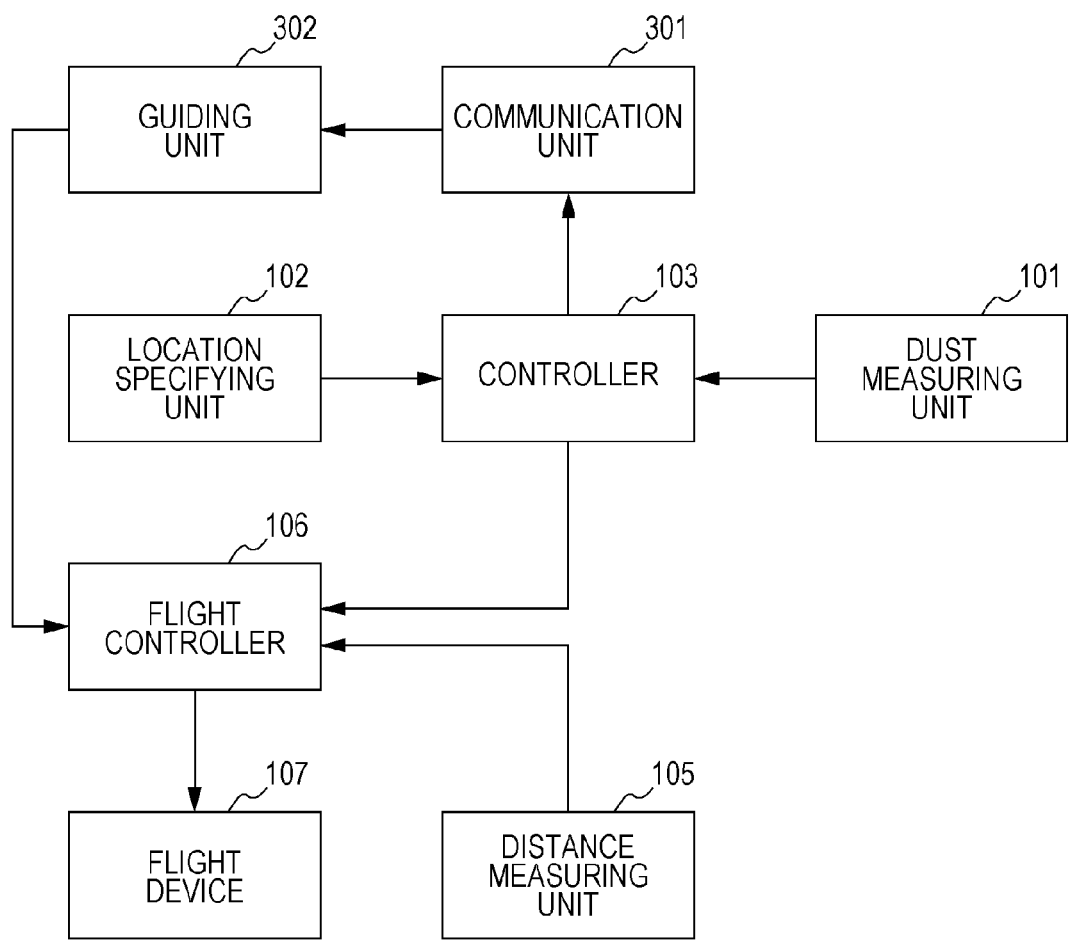
FIG. 7 is a block diagram illustrating a configuration of the dust detection apparatus according to a third exemplary embodiment of the present disclosure.

FIG. 7 is a block diagram illustrating a configuration of dust detection apparatus 300 according to the present exemplary embodiment. In FIG. 7, components identical to components used in the first exemplary embodiment (FIG. 2) have identical reference symbols, and description of the components will be omitted.

In dust detection apparatus 300 illustrated in FIG. 7, communication unit 301 receives information (guiding information) for guiding the user to the dust accumulation position, via an antenna from a server (not illustrated), in addition to an operation of communication unit 104 (FIGS. 1A and 1B). Communication unit 301 outputs the guiding information to guiding unit 302.

The guiding information includes, for example, a location that indicates the dust accumulation position, an amount of dust accumulation, and user information. The amount of dust accumulation may be a value that represents an actual amount of accumulation, and may be information that represents the actual amount of accumulation that is classified into ranks such as "large", "normal", and "small" (for example, see FIG. 8). The user information may include, for example, the current location of the user, or a distance between the user and the dust accumulation position (for example, see FIG. 8). When there is a plurality of dust accumulation positions to which the user is to be guided, the guiding information includes information about each of the plurality of dust accumulation positions.

Guiding unit 302 guides the user from the current location of the user to the dust accumulation position based on the guiding information received from communication unit 301. For example, first, guiding unit 302 instructs flight controller 106 to move dust detection apparatus 300 to the current location of the user. Guiding unit 302 then instructs flight controller 106 to move dust detection apparatus 300 to the dust accumulation position indicated by the guiding information. In guiding the user, guiding unit 302 may notify the user that the user will be guided to the dust accumulation position with a synthetic voice.

[Operation of Dust Detection Apparatus 300]

An operation of dust detection apparatus 300 thus configured will be described.

Methods 1 to 3 for guiding the user to the dust accumulation position in dust detection apparatus 300 will be exemplified below.

<Method 1>

In method 1, guiding unit 302 of dust detection apparatus 300 first instructs flight controller 106 to move dust detection apparatus 300 to the current location of the user indicated by the guiding information. Then, after dust detection apparatus 300 moves to the current location of the user, guiding unit 302 instructs flight controller 106 to move dust detection apparatus 300 to the dust accumulation position indicated by the guiding information. For example, guiding unit 302 instructs flight controller 106 to move dust detection apparatus 300 to the dust accumulation position at a speed at which the user can move.

In addition, guiding unit 302 includes, for example, a speaker. In guiding the user to the dust accumulation position, guiding unit 302 notifies the user that the user will be guided to the dust accumulation position with a synthetic voice. When the user permits guidance to the dust accumulation position, guiding unit 302 starts guidance to the dust accumulation position.

Guiding unit 302 may include, for example, a microphone to acquire information about whether the user permits guidance to the dust accumulation position. Alternatively, guiding unit 302 may acquire, through operational input into a device appliance retained by the user, the information about whether the user permits guidance to the dust accumulation position directly from the device appliance, or may acquire the information via the server.

<Method 2>

In method 2, the guiding information includes the plurality of dust accumulation positions to which the user is to be guided. The server arranges information about each of the plurality of dust accumulation positions in order in which dust detection apparatus 300 guides the user based on dust information received from dust detection apparatus 300.

For example, it is assumed that the amount of dust accumulation at each accumulation position is classified into ranks, such as "large", "normal", and "small", as described above. In this case, the server may determine a most efficient guiding order from among sets that each include dust accumulation positions of an identical rank, based on a distance from the current location of the user and on the amount of dust accumulation. That is, the server determines the guiding order to the dust accumulation positions in each set, based on the amount of dust accumulation and on a moving distance of the user. For example, the server may determine the guiding order from among the sets that each include dust accumulation positions of an identical rank in accordance with a traveling salesman problem solution algorithm.

For example, the guiding information is arranged in order of a set of "large", a set of "normal", and a set of "small". In this case, guiding unit 302 guides the user to the dust accumulation positions in order from the set with the larger amount of dust. Specifically, guiding unit 302 sequentially guides the user to the dust accumulation positions included in the set of "large", then sequentially guides the user to the dust accumulation positions included in the set of "normal", and finally, sequentially guides the user to the dust accumulation positions included in the set of "small".

For example, if the user is simply guided to the dust accumulation positions in decreasing order of the amount of dust, the user may travel back and forth many times in a room. This will exhaust the user. In contrast, taking into consideration the amount of dust and the moving distance of the user, dust detection apparatus 300 can guide the user so that the user can efficiently move to the dust accumulation position (dust accumulation position having higher priority) at which dust should be removed earlier.

Dust detection apparatus 300 may perform determination processing of the guiding order in the guiding information. The determination of the guiding order is not limited to determination made for each set of an identical rank. For example, the guiding order may be determined from among both sets of "large" and "normal" in accordance with the traveling salesman problem solution algorithm. In this case, guiding unit 302 guides the user to the dust accumulation positions included in the set of "large" and the set of "normal" sequentially, and then guides the user to the dust accumulation positions included in the set of "small" sequentially. This allows presentation of efficient cleaning order to the user who can secure only limited time (a short time such as 10 minutes) for cleaning.

<Method 3>

In method 3, before starting guidance to the dust accumulation positions, guiding unit 302 presents the dust accumulation positions to the user. Guiding unit 302 then starts guidance to the dust accumulation positions that need guidance according to instructions by the user. That is, guiding unit 302 guides the user to the positions that the user selects from among the dust accumulation positions detected by controller 103.

The dust accumulation positions may be presented to the user, for example, with a synthetic voice using the speaker (not illustrated) included in guiding unit 302. The dust accumulation positions may be presented to the user by dust detection apparatus 300 directly sending to the device appliance retained by the user. The dust accumulation positions may be presented to the user by dust detection apparatus 300 sending to the device appliance retained by the user via the server.

Guiding unit 302 may determine whether the user requires guidance (selection result of the dust accumulation positions) by, for example, acquiring a voice of the user using the microphone (not illustrated) included in guiding unit 302, and through speech recognition processing. Alternatively, guiding unit 302 may receive information about whether the user requires guidance directly from the device appliance retained by the user, and may receive the information from the device appliance retained by the user via the server.

Thus, in method 3, the user selects the dust accumulation positions to which the user causes dust detection apparatus 300 to guide the user. That is, the user determines order of positions to clean. This allows the user to efficiently solve a problem unique to the user. For example, if a family member who is suffering a pollen allergy often approaches a position presented as the dust accumulation position, the user can cause dust detection apparatus 300 to guide the user to the dust accumulation position with priority.

Methods 1 to 3 for guiding the user to the dust accumulation positions in dust detection apparatus 300 have been described above.

Thus, according to the present exemplary embodiment, dust detection apparatus 300 guides the user to the detected dust accumulation positions, so that the user can accurately specify and efficiently clean the dust accumulation positions even if the dust accumulation positions are hard for the user to recognize.

According to the present exemplary embodiment, for example, when guiding the user to the positions at which the dust measurement value exceeds a predetermined threshold (first threshold), dust detection apparatus 300 may attract attention of the user that the amount of dust is large. Methods for attracting attention may include, for example, providing dust detection apparatus 300 with a light emitting element to blink the light emitting element, and notifying the user with a synthetic voice. This can cause the user to intuitively recognize a position at which dust is likely to accumulate, and can urge the user to do the cleaning frequently.

On the other hand, dust detection apparatus 300 may, for example, guide the user to a position at which the dust measurement value is less than a predetermined threshold (first threshold or other second threshold). Then, dust detection apparatus 300 may notify the user that the amount of dust accumulation is small. Methods for notification may include, for example, providing dust detection apparatus 300 with a light emitting element to blink the light emitting element, and dust detection apparatus 300 may praise the user with a synthetic voice. This allows the user to intuitively recognize extent of dust accumulation.

In addition, according to the present exemplary embodiment, after guiding the user to the dust accumulation position, dust detection apparatus 300 may evacuate to somewhere else while the user is cleaning the dust accumulation position guided by dust detection apparatus 300. This allows dust detection apparatus 300 to avoid becoming obstructive to the user's cleaning operation, and to prevent propulsive airflow of dust detection apparatus 300 from stirring up dust collected by the user.

Each of the exemplary embodiments of the present disclosure has been described above.

In each of the exemplary embodiments described above, a description has been given of a case where the dust detection apparatus (FIGS. 1A and 1B or FIGS. 4A and 4B) is a small helicopter-shaped apparatus that has propellers. However, the dust detection apparatus is not limited to the apparatus that has propellers, and may be an airship that has a balloon, for example. In this case, the dust detection apparatus may further include a brush for stirring up dust when measuring the amount of dust. This allows the dust detection apparatus to prevent airflow needed for a flight from stirring up dust more than necessary.

In each of the exemplary embodiments described above, a description has been given of a case where the dust detection apparatus includes the dust measuring unit. However, the dust detection apparatus may not include the dust measuring unit described above, and may include, for example, an adhesive tape. In this case, the dust detection apparatus may acquire dust with the tape and return to a storage device (not illustrated) for the dust detection apparatus, and the storage device may detect dust by analyzing the dust adhering to the tape. This eliminates the need for the dust detection apparatus to include the dust measuring unit, and makes it possible to downsize the dust detection apparatus and to reduce power consumption.

In each of the exemplary embodiments described above, a description has been given of a case where the present disclosure is implemented by hardware as an example, but the present disclosure can also be implemented by software in cooperation with hardware.

Each of functional blocks (FIG. 2, FIG. 5, FIG. 7) used for the description of each of the above exemplary embodiments is typically implemented as an LSI (Large-Scale Integration) circuit that is an integrated circuit. These functional blocks may be formed as separate chips, or some or all of the functional blocks may be included in one chip. Although the integrated circuit is called LSI here, the integrated circuit may be referred to as an IC, a system LSI, a super LSI, and an ultra LSI, depending on a difference in a degree of integration.

Methods for circuit integration are not limited to LSI, and may be implemented by using a dedicated circuit or a general-purpose processor. Circuit integration may use an FPGA (Field Programmable Gate Array) that is programmable after manufacture of an LSI, or a reconfigurable processor in which connections or settings of circuit cells within the LSI are reconfigurable.

Furthermore, if an advance in a semiconductor technology or another related technology yields a circuit integration technology that may substitute for LSI, the functional blocks may be obviously integrated by using such a technology. Biotechnology may be applied.

An overview of one aspect of the present disclosure is as follows.

The dust detection apparatus according to one aspect of the present disclosure includes: a dust measuring unit that measures an amount of dust in air; a controller that determines a moving direction of the dust detection apparatus based on the measured amount of dust or a predetermined dust accumulation position candidate; a flight controller that controls a flight of the dust detection apparatus to the determined moving direction; and a communication unit that sends, to a server, location information of a dust accumulation position determined based on the measured amount of dust, and the amount of dust measured by the dust measuring unit at the dust accumulation position.

The dust measuring unit may measure the amount of dust at a current location in a plurality of directions, and the controller may determine, as the moving direction, the direction in which the amount of dust is largest from among the plurality of directions.

When the amount of dust measured this time is equal to or less than the amount of dust measured last time, the controller may determine, as the dust accumulation position, a current location at which the dust detection apparatus measures the amount of dust this time.

The dust detection apparatus may further include a storage that stores a plurality of positions that are each the dust accumulation position candidate, and the controller may sequentially select each of directions to the plurality of positions as the moving direction, and the dust measuring unit may measure the amount of dust at each of the plurality of positions.

The dust measuring unit may measure the amount of dust at a current location in a plurality of directions, and when the amount of dust at the current location exceeds a threshold, the controller may postpone movement to the plurality of positions that are each the dust accumulation position candidate, and determine, as the moving direction, the direction in which the amount of dust is largest from among the plurality of directions.

The dust detection apparatus may further include a furniture shape grasp unit that grasps a shape of indoor furniture, and furniture having a large cross section viewed in a vertical direction may be determined as the dust accumulation position candidate.

The dust detection apparatus may further include a guiding unit that guides a user to the dust accumulation position.

When there is the plurality of dust accumulation positions, the server may divide the plurality of dust accumulation positions into a plurality of sets based on the amount of dust, and the guiding unit may guide the user in order from the dust accumulation positions included in each of the sets having the larger amount of dust.

When there is the plurality of dust accumulation positions, the server may determine a guiding order to the dust accumulation positions based on the amount of dust and on a moving distance of the user to the dust accumulation positions.

The guiding unit may guide the user to a position that the user selects from among the dust accumulation positions.

The dust detection apparatus may further include a straw-shaped dust collecting unit that takes air into the dust measuring unit from a distal end of the straw shape.

A dust detection method according to one aspect of the present disclosure is a dust detection method using a dust detection apparatus, the dust detection method includes: measuring an amount of dust in taken air; determining a moving direction of the dust detection apparatus based on the measured amount of dust or a predetermined dust accumulation position candidate; controlling a flight of the dust detection apparatus to the determined moving direction; and sending, to a server, location information of a dust accumulation position determined based on the measured amount of dust and the amount of dust measured by the dust measuring unit at the dust accumulation position.

The present measurement is useful in the dust detection apparatus or the like capable of detecting dust accumulated on high places, such as a ceiling, a wall, and furniture.

What is claimed is:

1. A dust detection apparatus comprising:
a memory that stores predetermined dust accumulation candidate positions, including a first position and a second position;
a dust sensor that measures a first plurality of air dust amounts at the first position in a plurality of directions, the first plurality of air dust amounts including a first air dust amount at the first position in a first direction of the plurality of directions;
a controller that determines a moving direction of the dust detection apparatus, the moving direction being a direction directed toward the second position, when the first plurality of air dust amounts do not exceed a threshold, and the moving direction being the first direction when the first air dust amount exceeds the threshold and is the largest of the first plurality of the air dust amounts;
a flight controller that controls a flight of the dust detection apparatus to the determined moving direction; and
a communicator that sends, to a server, location information of a dust accumulation position an air dust amount at the dust accumulation position,
wherein the dust sensor further measures a second plurality of air dust amounts at a location during movement of the dust detection apparatus in the first direction, and
when the second plurality of air dust amounts are less than the first plurality of air dust amounts, the controller determines the location as the dust accumulation position, and changes the moving direction from the first direction to the direction directed toward the second position.

2. A dust detection apparatus comprising:
a dust sensor that measures an amount of dust in air;
a controller that determines a moving direction of the dust detection apparatus based on the measured amount of dust or a predetermined dust accumulation candidate position;
a flight controller that controls a flight of the dust detection apparatus to the determined moving direction; and
a communicator that sends, to a server, location information of a dust accumulation position determined based on the measured amount of dust, and the amount of dust measured by the dust sensor at the dust accumulation position,
a furniture shape sensor that detects a shape of indoor furniture,
wherein furniture having a large cross section viewed in a vertical direction is determined as the dust accumulation candidate position, based on the detected shape of indoor furniture.

3. The dust detection apparatus according to claim 1, further comprising:
a guiding processor that guides a user to the dust accumulation position.

4. A dust detection apparatus comprising:
a dust sensor that measures an amount of dust in air;
a controller that determines a moving direction of the dust detection apparatus based on the measured amount of dust or a predetermined dust accumulation candidate position;
a flight controller that controls a flight of the dust detection apparatus to the determined moving direction;
a communicator that sends, to a server, location information of a dust accumulation position determined based on the measured amount of dust, and the amount of dust measured by the dust sensor at the dust accumulation position; and
a guiding processor that guides a user to the dust accumulation position,
wherein, when there is a plurality of dust accumulation positions, the server divides the plurality of dust accumulation positions into a plurality of sets based on the amount of dust, and
the guiding processor guides the user in order from the dust accumulation positions included in each of the plurality of sets having the larger amount of dust.

5. The dust detection apparatus according to claim 4, wherein, the server determines a guiding order to the dust accumulation positions based on the amount of dust and on a moving distance of the user to the dust accumulation positions.

6. The dust detection apparatus according to claim 4, wherein the guiding processor guides the user to a position that the user selects from the dust accumulation positions.

7. A dust detection apparatus comprising:
a dust sensor that measures an amount of dust in air;
a controller that determines a moving direction of the dust detection apparatus based on the measured amount of dust or a predetermined dust accumulation candidate position;
a flight controller that controls a flight of the dust detection apparatus to the determined moving direction;
a communicator that sends, to a server, location information of a dust accumulation position determined based on the measured amount of dust, and the amount of dust measured by the dust sensor at the dust accumulation position; and
a straw-shaped dust collector that takes air into the dust sensor from a distal end of the straw shape,
wherein the straw-shaped dust collector is extendable and retractable downwardly from a body of the dust detection apparatus such that the distal end of the straw-shaped dust collector protrudes in an oblique direction to an outside of an area directly below a bottom of the body of the dust detection apparatus.

8. A dust detection method using a dust detection apparatus, the dust detection method comprising:

storing predetermined dust accumulation candidate positions, including a first position and a second position;

measuring a first plurality of air dust amounts at the first position in a plurality of directions, the first plurality of air dust amounts including a first air dust amount at the first position in a first direction of the plurality of directions;

determining a moving direction of the dust detection apparatus, the moving direction being a direction directed toward the second position, when the first plurality of air dust amounts do not exceed a threshold, and the moving direction being the first direction when the first air dust amount exceeds the threshold and is the largest of the first plurality of the air dust amounts;

controlling a flight of the dust detection apparatus in the determined moving direction;

measuring a second plurality of air dust amounts at a location during movement of the dust detection apparatus in the first direction, determining, when the second plurality of air dust amounts are less than the first plurality of air dust amounts, the location as a dust accumulation position, and changing the moving direction from the first direction to the direction directed toward the second position; and sending, to a server, location information of the dust accumulation position an air dust amount at the dust accumulation position.

9. A dust detection method using a dust detection apparatus, the dust detection method comprising:
measuring an amount of dust in air by a dust sensor;
determining, by a processor of the dust detection apparatus, a moving direction of the dust detection apparatus based on the measured amount of dust or a predetermined dust accumulation candidate position;
controlling, by the processor, a flight of the dust detection apparatus to the determined moving direction; and
sending, by the processor, to a server, location information of a dust accumulation position determined based on the measured amount of dust, and the measured amount of dust at the dust accumulation position;
detecting a shape of indoor furniture; and
determining furniture having a large cross section viewed in a vertical direction as the dust accumulation candidate position, based on the detected shape of indoor furniture.

10. A dust detection method using a dust detection apparatus, the dust detection method comprising:
measuring an amount of dust in air by a dust sensor;
determining, by a processor of the dust detection apparatus, a moving direction of the dust detection apparatus based on the measured amount of dust or a predetermined dust accumulation candidate position;
controlling, by the processor, a flight of the dust detection apparatus to the determined moving direction; and
sending, by the processor, to a server, location information of a dust accumulation position determined based on the measured amount of dust, and the measured amount of dust at the dust accumulation position; and
guiding, by the processor, a user to the dust accumulation position; and
dividing, by the server, a plurality of dust accumulation positions into a plurality of sets based on amounts of dust for the plurality of dust accumulation positions, the dust accumulation position being one of the plurality of dust accumulation position,
wherein the user is guided in order from the dust accumulation positions included in each of the plurality of sets having the larger amount of dust.

11. The dust detection method according to claim 10, further comprising:
determining, by the server, a guiding order to the plurality of dust accumulation positions based on amounts of dust for the plurality of dust accumulation positions and on moving distances of the user to the dust accumulation positions, the dust accumulation position being one of the plurality of dust accumulation position.

12. The dust detection method according to claim 10,
wherein the user is guided to a position that the user selects from the dust accumulation positions.

13. A dust detection method using a dust detection apparatus, the dust detection method comprising:
measuring an amount of dust in air by a dust sensor;
determining, by a processor of the dust detection apparatus, a moving direction of the dust detection apparatus based on the measured amount of dust or a predetermined dust accumulation candidate position;
controlling, by the processor, a flight of the dust detection apparatus to the determined moving direction; and
sending, by the processor, to a server, location information of a dust accumulation position determined based on the measured amount of dust, and the measured amount of dust at the dust accumulation position; and
taking air into the dust sensor from a distal end of a straw-shaped dust collector,
wherein the straw-shaped dust collector is extendable and retractable downwardly from a body of the dust detection apparatus such that the distal end of the straw-shaped dust collector protrudes in an oblique direction to an outside of an area directly below a bottom of the body of the dust detection apparatus.

* * * * *